United States Patent
Mueller et al.

[11] Patent Number: 6,149,994
[45] Date of Patent: Nov. 21, 2000

[54] POLYMERISABLE POLYAMIDE DERIVATIVES

[75] Inventors: Egbert Mueller, Erzhausen; Hans-Dieter Harders, Darmstadt; Dieter Lubda, Bensheim, all of Germany

[73] Assignee: Merck Patent Gesellschaft mit beschrankter Haftung, Germany

[21] Appl. No.: 09/194,121

[22] PCT Filed: May 28, 1997

[86] PCT No.: PCT/EP97/02768

§ 371 Date: Nov. 23, 1998

§ 102(e) Date: Nov. 23, 1998

[87] PCT Pub. No.: WO97/49754

PCT Pub. Date: Dec. 31, 1997

[30] Foreign Application Priority Data

Jun. 21, 1996 [DE] Germany .......................... 196 24 813
Jul. 6, 1996 [DE] Germany .......................... 196 27 404
Jul. 17, 1996 [DE] Germany .......................... 196 28 832
Jul. 19, 1996 [DE] Germany .......................... 196 29 206

[51] Int. Cl.[7] .......................... B29D 22/00; B29D 23/00; B32B 1/08

[52] U.S. Cl. .................. 428/35.7; 428/308.4; 428/319.3; 428/319.7; 525/426

[58] Field of Search ............................... 428/35.7, 308.4, 428/319.3, 319.7; 525/426

[56] References Cited

U.S. PATENT DOCUMENTS 4,563,507  1/1986  Dyer ........................................ 525/426
4,595,730  6/1986  Blondel et al. ......................... 525/178

FOREIGN PATENT DOCUMENTS 0143037  10/1984  European Pat. Off. .
0147267  11/1984  European Pat. Off. .
143037   5/1985   European Pat. Off. .
147267   7/1985   European Pat. Off. .
4129901  3/1993   Germany .

OTHER PUBLICATIONS

English Abstract for EP147267.
English Abstract for DE4129901.

*Primary Examiner*—Ana Woodward
*Attorney, Agent, or Firm*—Millen, White, Zelano & Branigan, P.C.

[57] ABSTRACT

The invention relates to polyamides which are derivatized with polymerizable double bonds and are obtainable by reaction of the amino groups of the polyamide with an amino-reactive compound which contains a polymerizable double bond, or by reaction of the carboxyl groups of the polyamide with a carboxyl group-reactive compound which contains a polymerizable double bond. Examples of amino-reactive compounds which contain a polymerizable double bond are the anhydrides of ethylenically unsaturated carboxylic acids, such as acrylic acid chloride or anhydride, methacrylic acid chloride or anhydride, or vinylazlactone derivatives. An example of a carboxyl group-reactive compound is allylamine.

These derivatized polyamides can be converted into polymer-modified base polymers (typically block polymers) with improved properties. These polymer-modified base polymers are suitable as adsorbents for chromatography and as carriers for enzymes.

18 Claims, No Drawings

POLYMERISABLE POLYAMIDE DERIVATIVES

The invention relates to polymerizable derivatives of polyamides and processes for the polymerization of polyamides derivatized in this way, and finally to polymers and shaped articles prepared by these processes.

The patent applications DE 195 01 726 and WO 96/22316 disclose polymerizable derivatives of polyamides and processes for the polymerization of polyamides derivatized in this way. The following reaction steps are carried out for this:

1. Reaction of the amino groups of a polyamide or of a shaped article of polyamide with a solution of a compound which contains a double bond, the reaction with the amino groups taking place via an oxirane group; polymerizable derivatives of the polyamide are formed by this reaction;
2. Polymerization of monomers, by customary processes, onto the double bonds inserted in the first step, a block polymer being formed which contains, if appropriate, the reactive groups introduced with the monomers, preferred reactive groups being, in particular, oxirane groups or groups which can be converted into azlactones;
3. Optional polymer-analogous reaction of the reactive groups from step 2 to give a separating material or an immobilized catalyst or enzyme.

If chiral compounds are used for these reactions, chirally modified shaped articles which are suitable for enantiomer separations are accessible.

There is therefore the object of providing further, in particular alkali-stable, polymerizable derivatives of polyamide or shaped articles of polyamide.

It has been found that instead of the derivatizing agents disclosed in DE 195 01 726 and WO 96/22 316 for the first reaction step, further derivatizing agents can be used. These also include derivatizing agents which allow the reaction of carboxyl groups in the polyamide in an analogous manner. It has been found here that some of these derivatizing agents lead to derivatives which have an improved stability in the presence of alkaline solutions. It has furthermore been found that the density of the polymerizable groups can be increased if carboxyl groups present in the base material are reacted with a diamine. In an analogous manner, the density of the polymerizable groups can,be increased by reacting the base polymer (polyamide) with dicarboxylic acids or dicarboxylic acid anhydrides. The carboxyl groups are then reacted with an amino compound which contains unsaturated groups, and polymerizable groups are introduced in this way.

The invention relates to polyamides which are derivatized with polymerizable double bonds and are obtainable by reaction of a coupling group of the polyamide with an ethylenically unsaturated derivatizing agent. According to the invention, the term "coupling groups of the polyamide" is understood as meaning the amino or carboxyl groups of the polyamide. In commercially available polyamides, the terminal amino or carboxyl groups are therefore the coupling groups. According to the invention, the term "ethylenically unsaturated derivatizing agent" is understood as meaning reagents or combinations of reagents which react with the coupling groups of the polyamide, that is to say with the carboxyl or with the amino groups, and as a result introduce ethylenically unsaturated groupings into the product formed.

Examples of suitable derivatizing agents which react with amino groups are disclosed in DE 195 01 726 and WO 96/22316. Polyamides which are derivatized with polymerizable double bonds and are obtainable by reaction of amino-reactive compounds containing an oxirane ring and an ethylenically unsaturated double bond are therefore not the subject matter of the invention if the base polymer is reacted without having first being reacted with a diamino compound.

New suitable derivatizing agents are, for example: anhydrides of an ethylenically unsaturated carboxylic acid, for example methacrylic acid anhydride or chloride, acrylic acid anhydride or chloride, or vinylazlactone derivatives of the formula I

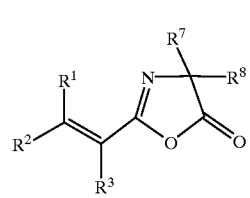

wherein $R^1$, $R^2$ and $R^3$ independently of one another are H or $CHO_3$;

$R^7$ and $R^8$ independently of one another are H or $C_1$- to $C_5$-alkyl.

Preferably, $R^1$, $R^2$ and $R^3$ are H and $R^7$ and $R^8$ are methyl.

The ethylenically unsaturated derivatizing agents also include those which react with the carboxyl groups and introduce ethylenically unsaturated groups in this way. This group of ethylenically unsaturated derivatizing agents includes, for example, allylamine, which, for example, can be bonded to carboxyl groups of the polyamide by reaction with carbodiimides.

It is also possible to carry out a reaction of coupling groups of the polyamide with a bifunctional derivatizing agent before the reaction with the ethylenically unsaturated derivatizing agent. Thus, for example, additional amino groups are introduced into the polyamide by reaction of carboxyl groups of the polyamide with, diamino compounds. Conversely, it is also possible to introduce additional carboxyl groups by reaction of the amino groups of the polyamide with dicarboxylic acids or dicarboxylic acid anhydrides.

The invention also relates to polymer-modified materials obtainable by polymerization of monomers onto a polyamide, as the base polymer, which has been derivatized according to the invention with polymerizable double bonds. Particularly preferred polymers are those which contain acrylic acid as the monomer or monomer units of the formula II, III, IV or V:

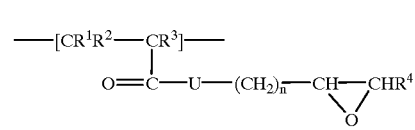

In formula II:

$R^1$, $R^2$ and $R^3$ independently of one another are H or $CH_3$, $R^4$ is H, alkyl having 1–5 C atoms or aryl having 6–12 C atoms, U is —O— or —NH— and n is an integer between 1 and 5.

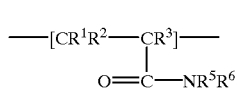   III

In formula III:

R$^1$, R$^2$ and R$^3$ independently of one another are H or CH$_3$,

R$^5$ is H, alkyl having 1–5 C atoms which is substituted by —COOH, by —SO$_3$H, by —NR$^7$R$^8$ or by —N$^+$R$^7$R$^8$R$^9$, or aryl having 6–12 C atoms which is substituted by —COOH, by —SO$_3$H, by —NR$^7$R$^8$ or by —N$^+$R$^7$R$^8$R$^9$, R$^6$ is alkyl having 1–5 C atoms which is substituted by —COOH, by —SO$_3$H, by —NR$^7$R$^8$ or by —N$^+$R$^7$R$^8$R$^9$, or aryl having 6–1 C atoms which is substituted by —COOH, by —SO$_3$H, by —NR$^7$R$^8$ or by —N$^+$R$^7$R$^8$R$^9$, wherein $^5$ and R$^6$ are co-ordinated such that either both radicals are acid or basic or one of the radicals is neutral, R$^7$ and R$^8$ independently of one another are H or alkyl having 1–5 C atoms and R$^9$ is alkyl having 1–5 C atoms.

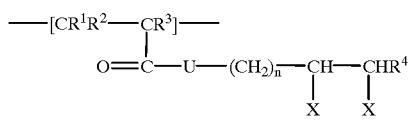   IV

In formula IV:

R$^1$, R$^2$ and R$^3$ independently of one another are H or CH$_3$,

R$^4$ is H, alkyl having 1–5 C atoms or aryl having 6–12 C atoms,

U is —O— or —NH—, n is an integer between 1 and 5 and one radical X is a separation effector and the other radical X is OH.

The separation effector can have, in particular, one of the following meanings:

a) an ionic group chosen from —PO$_4$H$_2$, —SO$_3$H, —NR$^7$R$^8$ or —N$^+$R$^7$R$^8$R$^9$, wherein R$^7$ and R$^8$ independently of one another are H or alkyl having 1–5 C atoms and R$^9$ is alkyl having 1–5 C atoms, with the proviso that if X=—N$^+$R$^7$R$^8$R$^9$, R$^7$ and R$^8$ cannot be H, b) a hydrophobic grouping —OR$^{10}$ or —NHR$^{10}$, wherein R$^{10}$ is C$_1$–C$_{20}$-alkyl, C$_6$–C$_{25}$-aryl, C$_7$–C$_{25}$-alkylaryl or C$_7$–C$_{25}$-arylalkyl, and wherein these radicals can also be derivatized with nitrile or C$_1$–C$_5$-alkoxy, and wherein also one or more non-adjacent CH$_2$ groups can be replaced by NH or O, or also one or more CH groups can be replaced by N;

c) a metal chelate grouping;

d) a thiophilic radical;

e) a chiral radical.

Thiophilic radicals are disclosed, for example, in EP 0 165 912.

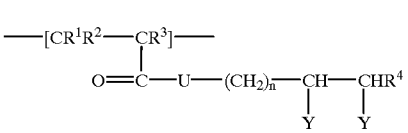   V

In formula V:

R$^1$, R$^2$ and R$^3$ independently of one another are H or CH$_3$,

R$^4$ is H, alkyl having 1–5 C atoms or aryl having 6–12 C atoms, n is an integer between 1 and 5, U is —O— or —NH—, one radical Y is a radical of the formula VI and the other radical Y is OH

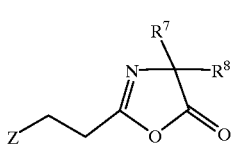   VI

Z is —S or —NH and

R$^7$ and R$^8$ independently of one another are H or alkyl having 1–5 C atoms.

The polymer-modified materials which contain monomer units of the formula II or V can be used in particular for the preparation of affinity supports or for immobilization of enzymes.

The invention therefore also relates to affinity supports and immobilized enzymes which can be prepared from a polymer-modified material according to the invention.

Porous and non-porous shaped articles of polyamides are known; these include, for example, membranes, sponges, hoses and hollow fibre membranes. The invention therefore also relates to such shaped articles which substantially comprise a polymer-modified material according to the invention and which additionally can also comprise affinity ligands or immobilized enzymes.

According to the invention, unsaturated radicals are introduced into the polyamide in the first reaction step. For this, in addition to the reaction sequences known from DE 195 01 726, the reaction sequences disclosed below can be used. A common feature of these reaction sequences is that an ethylenically unsaturated derivatizing agent, that is to say an amino- or carboxyl-reactive compound which contains a polymerizable double bond, is reacted with the amino or carboxyl groups of the polyamide. A large number of amino-reactive compounds are known in principle to the expert. These include, for example, oxirane derivatives, acid anhydrides, acid azides and azlactone derivatives. Reaction sequences which are used in peptide syntheses can be used in a similar manner, for example reactions with agents which split off water (for example carbodiimides), or the use of activated esters (for example p-nitrophenyl esters). In an analogous manner, it is possible to derivatize the free carboxyl groups of polyamides, so that these are likewise available as starting points for a polymerization. Compounds which can react with carboxyl groups and contain polymerizable double bonds, for example allylamine, can be used for this.

If the base polymer contains both carboxyl and amino groups, it is possible to increase the loading density by carrying out a reaction with a bifunctional derivatizing agent, that is to say with a diamino compound or with a dicarboxylic acid or a dicarboxylic acid anhydride, before the reaction with the ethylenically unsaturated derivatizing agent. Thus, for example, additional amino groups, which can be further reacted as described above, can be introduced into the base polymer by reaction with 1,2-ethylenediamine. Particularly preferred diamino compounds are α,ω-diaminoalkanes, such as, for example, 1,2-ethylenediamine, 1,3-diaminopropane, 1,4-diaminobutane or 1,6-diaminohexane. It is also possible to react the amino groups of the polyamide with a dicarboxylic acid or a dicarboxylic acid anhydride, in order then to insert polymerizable double bonds on the carboxyl groups with amino compounds which contain polymerizable double bonds, for example allylamine.

Reaction sequences for the reactions mentioned are known to the expert, and also include, in particular, reactions with agents which split off water, or reactions in which one of the reaction partners is present in activated form. For example, the reaction is carried out using carbodiimides or by activation of the carboxyl groups as an acid azide. The reaction with water-soluble carbodiimides, such as, for example, 1-ethyl-3-(3-dimethylaminopropyl)-carbodiimide (EDC), in aqueous or organic-aqueous solutions, which are preferably buffered, is preferred here. Preferred buffer substances are sodium acetate or morpholine-ethanesulfonic acid. The pH in such reactions is usually between 4 and 6.

Polyamides which are suitable as the base polymer are known to the expert and are also commercially obtainable. These include, for example, the polymers known under the tradename NYLON®, for example NYLON® 66 and NYLON® 6. Porous or non-porous shaped articles consisting of such polyamides are also known and also commercially obtainable; these include, for example, beaded shaped articles, membranes, hoses, hollow fibre membranes and sponges. The reaction of such shaped articles is preferred, since under the reaction conditions such as are used in DE 195 01 726 (reaction temperature below 60° C.), their shape is retained, while other processes for the derivatization of polyamide are carried out in the melt or in solution.

The reaction with the anhydrides of ethylenically unsaturated carboxylic acids is carried out by known processes, for example the Schotten-Baumann process at temperatures below 60° C.; polymerizable derivatives of polyamides are formed by this reaction. According to the invention, the term anhydrides of ethylenically unsaturated carboxylic acids is understood as meaning both the simple and the mixed anhydrides. The first group includes, for example, acrylic anhydride and methacrylic anhydride, and the second group includes, for example, acid chlorides, such as acryloyl chloride and methacryloyl chloride. Further examples of ethylenically unsaturated carboxylic acids are crotonic acid, isocrotonic acid, vinylacetic acid and also sorbic acid. Preferred anhydrides of ethylenically unsaturated carboxylic acids are acryloyl chloride, methacryloyl chloride, acrylic anhydride and methacrylic anhydride.

The reaction of the amino groups of the polyamide with a vinylazlactone derivative of the formula I

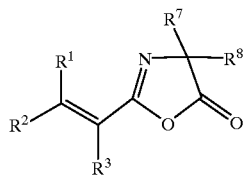

wherein
$R^1$, $R^2$ and $R^3$ independently of one another are H or $CH_3$;
$R^7$ and $R^8$ independently of one another are H or $C_1$- to $C_5$-alkyl is carried out by processes known to the expert. Preferably, $R^1$, $R^2$ and $R^3$ are H and $R^7$ and $R^8$ are methyl; such vinylazlactone derivatives are commercially obtainable. Further vinylazlactone derivatives of the formula I are also commercially obtainable or accessible by standard processes.

The polyamides usually used, such as, for example, NYLON® 66 or NYLON® 6, contain only terminal free carboxyl and/or amino groups. In this case, a block polymer is formed in the polymerization with monomers onto the derivatized base polymer. If the base polymer also contains lateral free carboxyl and/or amino groups in addition to the terminal free carboxyl and/or amino groups, lateral polymerizable groups are additionally formed. In a subsequent polymerization, grafting then takes place in addition to the formation of the block polymer. According to the invention, block and graft polymers are together called polymer-modified base polymers or polymer-modified materials.

By the reaction of the polyamide such as is disclosed in the present application, unsaturated C=C groups are introduced into the polyamide, in a similar manner to that in DE 195 01 726. Further monomers can be polymerized onto these groups by generally known processes, a polymer-modified base polymer according to the invention being formed. The choice of these monomers depends on the proposed intended use of the derivatized membrane:

a) DE 38 11 042 (EP 0 337 144; U.S. Pat. No. 5,453,186) discloses, inter alia, monomers which are suitable for the preparation of ion exchangers; these include, for example, acrylic acid, N-(sulfo-ethyl)-acrylamide, 2-acrylamido-2-methylpropane-sulfonic acid, N,N-dimethylaminomethyl-acrylamide, N,N-diethylaminoethyl-acrylamide and trimethyl-ammoniumethylacrylamide.

Other monomers mentioned in this publication allow the binding of affinity ligands or of enzymes, or are suitable for reversed phase chromatography: these include, for example, acrylic acid, acrylamide, allylamine or acrylonitrile.

b) DE 43 10 964 (EP 0 565 978) discloses monomers that contain an oxirane ring, an azlactone ring or a grouping which can be converted into an azlactone ring. Polymers which contain such monomers are particularly suitable for bonding of affinity ligands or of enzymes. Affinity ligands are disclosed by way of example in DE 43 10 964.

DE 43 34 359 (WO 95/10 354) furthermore discloses processes for the preparation of polymers which are derived from poly(meth)acrylamides and in which the amide groups have an oxirane ring.

c) EP 0 249 078, EP 0202 770 and EP 0 448 823 disclose optically active monomers which can be polymerized onto the base polymers derivatized with polymerizable double bonds. This results in polymer-modified base polymers which can be used as chiral adsorbents.

The epoxide or azlactone groups in such polymers can furthermore be further reacted in an advantageous manner, as a result of which ion exchangers, thiophilic adsorbents or adsorbents for metal chelate or hydrophobic chromatography and also for chiral separations are provided. In these reactions, for example, phosphoric acid, ammonia, diethylamine, trimethylamine, sulfurous acid or else complexing agents, such as iminodiacetic acid, or chiral compounds, such as proteins, peptides or polysaccharide derivatives, are added onto the oxirane ring or the azlactone group; examples of such polymer-analogous reactions are:

a) The preparation of thiophilic adsorbents and of adsorbents for metal chelate chromatography is disclosed in DE 43 10 964 (EP 0 565 978).
b) DE 43 33 674 (WO 95/09 964) and DE 43 33 821 (WO 95/09 695) disclose such reactions, with the aid of which ion exchangers can be provided.
c) DE 43 23 913 (WO 95/02 820) describes adsorbents for hydrophobic interaction chromatography.

According to the invention, the groups which are introduced into the chromatographic support by the abovementioned processes and which are essential for the separation of the analytical material are together called separation effectors.

Details of the preparation of the various adsorbents and their use can be seen from the abovementioned publications; the disclosure of these publications in this respect is introduced into the present application by reference.

The reaction in which further monomers are polymerized onto the polyamide derivatized according to the invention can be carried out as disclosed in DE 195 01 726. Correspondingly, the membranes derivatized and polymer-modified according to the invention, which contain separation effectors on the chains which have been polymerized on, can be employed for separations of substances in a manner similar to that which is customary, for example, for particulate adsorbents with similar separation effectors. In respect of the preparation and use of polymer-modified polyamide derivatives, reference is made to the disclosure of publications DE 195 01 726 and WO 96/22316.

The following examples are intended to illustrate the subject matter of the invention in more detail; they are not a restriction of the subject matter according to the invention.

Even without further statements, it is assumed that an expert can utilize the above description in the broadest scope. The preferred embodiments are therefore to be interpreted merely as a descriptive and in no way as in any manner a limiting disclosure.

The complete disclosure of all the applications, patents and publications mentioned above and below and the corresponding applications DE 196 24 813.2, filed on 21.06.1996, DE 196 27 404.4, fixed on 06.07.1996, DE 196 28 832.0, filed on 17.07.1996 and DE 196 29 206.9, filed on 19.07.1996, are introduced into this application by reference.

EXAMPLES

In the following, room temperature is understood as meaning a temperature between 15 and 30° C.

Example 1

Reaction of a Polyamide with Ethylenediamine

To carry out the synthesis, a polyamide hollow fibre bundle of polyamide 6 is packed into a 300-10 mm chromatography column SUPERFORMANCE® (Merck KGaA). An inert pump is attached to this column. For the reaction, 10 mol of ethylenediamine and 0.2 mol of EDC are dissolved in 200 ml of 0.1 M sodium acetate buffer (pH 4.7) and pumped in circulation at a high speed (5 ml/minute) at room temperature for 5 hours. The derivatized membrane is then washed with 1 M phosphate buffer pH 7 and with water until neutral.

The starting material has a content of amino groups of 1.2 $\mu$mol/g; after the reaction, the content of amino groups is 12.3 $\mu$mol/g.

Example 2

Introduction of C=C bonds Into an Amino-derivatized Polyamide with Acryloyl Chloride In the apparatus described in Example 1, the membrane amino-derivatized according to Example 1 is treated with 200 ml of an aqueous solution (1 M acrylyl chloride in 1 M NaOH; pumping of the solution in circulation at 5 ml/min; one hour at 4° C.). The derivatized hollow fibre membrane is then washed with 1 M sodium phosphate buffer pH 7 and water until neutral.

Example 3

Introduction of C=C Bonds Into a Polyamide with Acrylyl Chloride

In the apparatus described in Example 1, a polyamide hollow fibre bundle of NYLON® is treated with 200 ml of an aqueous solution (1 M acrylyl chloride in 1 M NaOH; pumping of the solution in circulation at 5 ml/min; one hour at 4° C.). The derivatized hollow fibre membrane is then washed with 1 M sodium phosphate buffer pH 7 and water until neutral.

Example 4

Introduction of C=C Bonds Into a Polyamide with Vinyldimethylazlactone

In the apparatus described in Example 1, a polyamide hollow fibre bundle of NYLON® is treated with a solution of 100 ml of vinyldimethylazlactone in 100 ml of acetone at room temperature. It is then rinsed with acetone and toluene.

Example 5

Introduction of C=C bonds Into a Polyamide (reaction with allylamine)

To carry out the synthesis, a polyamide hollow 20 fibre bundle of polyamide 6 is packed into a 300-10 mm chromatography column SUPERFORMANCE® (Merck KGaA). An inert pump is attached to this column. For the reaction, 10 mol of allylamine and 0.2 mol of EDC are dissolved in 200 ml of 0.1 M sodium acetate buffer (pH 4.7) and the solution is pumped in circulation at a high speed (5 ml/minute) at room temperature for 5 hours. The derivatized membrane is then washed with 1 M phosphate buffer pH 7 and with water until neutral.

Block copolymers can be prepared by the processes disclosed in DE 195 01 726.9 from the membranes derivatized according to Examples 2 to 5. The following examples illustrate this reaction.

Example 6

Block Polymer with Monomer Units of Glycidyl Methacrylate

The hollow fibre membrane derivatized according to Example 3 is rinsed in the apparatus described there first with acetone and then with toluene (in each case 200 ml). A solution of 15 g of glycidyl methacrylate and 1 g of azoisobutyronitrile (polymerization initiator) in 200 ml of toluene is then pumped in circulation at 100° C. for one hour (flow rate: 2 ml/min). The derivatized hollow fibre membrane is then rinsed with toluene, acetone and water.

Example 7

Block Polymer with Monomer Units of a Chlorohydrin Derivative of the Acrylamide and Polymer-analogous Reaction to Give the Oxirane Derivative Instead of glycidyl methacrylate, the chlorohydrin derivative of the acrylamide is polymerized onto the membrane derivatized according to Example 4. The oxirane derivative is prepared by treatment with 1 M sodium hydroxide solution at 60° C. (5 hours). After cooling, the membrane is washed until neutral.

Details of the reaction sequence are disclosed in DE 43 34 359.

Separating materials or immobilized enzymes or immobilized catalysts can be prepared by the processes disclosed in DE 195 01 726 by polymer-analogous reaction by processes known per se from block polymers which are prepared according to the above Examples 6 and 7. The following example illustrates such a reaction.

Example 8

Production of an Anion Exchanger of the $SO_3^-$ type 10 g of sodium dihydrogen phosphate, 40 g of sodium sulfite and 10 g of tetrabutylammonium hydrogen sulfate are dissolved in 200 ml of water and the solution is brought to pH 8. In the apparatus described in the above examples, the hollow fibre bundle onto which epoxypropyl methacrylate has been polymerized according to Example 7 is treated with the aqueous solution (2.5 hours, 95° C., flow rate: 5 ml/min). It is then washed with water, 1 M sodium hydroxide solution, water, 1 M phosphate buffer, pH 7 and with water.

What is claimed is:

1. A shaped article comprising a polymer-modified polyamide shaped article produced by a method comprising:
   a) providing a polyamide shaped article having amino and carboxyl groups;
   b) optionally, reacting carboxyl groups of said polyamide shaped article with a diamino compound or reacting amino groups of said polyamide shaped article with a dicarboxylic acid or dicarboxylic acid anhydride;
   c) obtaining a polyamide shaped article modified with polymerizable double bonds by reacting the amino and/or carboxyl groups on the polyamide shaped article from step a) or step b) with at least one group reactive with amino groups or carboxyl groups on a compound which contains a polymerizable double bond in addition to the at least one group reactive with the amino groups or the carboxyl groups on the polyamide shaped article, provided that, if this compound contains a group reactive with the amino groups, it contains no oxirane ring unless the polyamide shaped article has been reacted with the diamino compound in b);
   d) polymerizing monomers onto at least one polymerizable double bond of the polyamide shaped article modified with polymerizable double bonds from c) to obtain the shaped article.

2. The shaped article of claim 1 prepared by further reacting the shaped article from d) to provide a separation effector group thereon.

3. The shaped article according to claim 1, wherein the carboxyl groups of the polyamide shaped article are reacted with a diamino compound in b).

4. The shaped article of claim 3, wherein the compound which contains a polymerizable double bond is an anhydride of an ethylenically unsaturated carboxylic acid and it is reacted with an amino group of the diamino-reacted polyamide shaped article.

5. The shaped article of claim 3, wherein the compound which contains a polymerizable double bond is a vinylazlactone of the formula I:

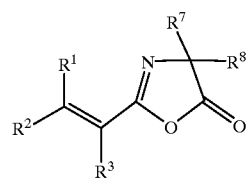

wherein
    $R^1$, $R^2$ and $R^3$ independently of one another are H or $CH_3$; and
    $R^7$ and $R^8$ independently of one another are H or $C_1$- to $C_5$-alkyl,
    and it is reacted with an amino group of the diamino-reacted polyamide shaped article.

6. The shaped article according to claim 1, wherein the amino groups of the polyamide shaped article are reacted with a dicarboxylic acid or a dicarboxylic acid anhydride in b).

7. The shaped article according to claim 1, wherein the compound which contains a polymerizable double bond is an anhydride of an ethylenically unsaturated carboxylic acid and it is reacted with an amino group of the polyamide shaped article.

8. The shaped article according to claim 1, wherein the compound which contains a polymerizable double bond is a vinylazlactone of the formula I

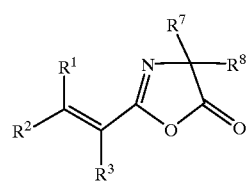

wherein
    $R^1$, $R^2$ and $R^3$ independently of one another are H or $CH_3$; and
    $R^7$ and $R^8$ independently of one another are H or $C_1$- to $C_5$-alkyl,
    and it is reacted with an amino group of the polyamide shaped article.

9. The shaped article according to claim 1, wherein the monomers polymerized in d) comprise acrylic acid monomer units.

10. The shaped article according to claim 1, wherein the monomers polymerized in d) comprise monomer units of the formula II:

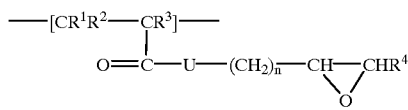

II wherein

R$^1$, R$^2$ and R$^3$ independently of one another are H or CH$_3$,

R$^4$ is H, alkyl having 1–5 C atoms or aryl having 6–12 C atoms,

U is —O— or —NH— and n is an integer from 1 to 5.

11. The shaped article according to claim 1, wherein the monomers polymerized in d) comprise monomer units of the formula V:

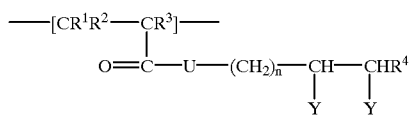

V wherein

R$^1$, R$^2$ and R$^3$ independently of one another are H or CH$_3$,

R$^4$ is H, alkyl having 1–5 C atoms or aryl having 6–12 C atoms,

U is —O— or —NH— n is an integer from 1 to 5, one radical Y is a radical of the formula VI and the other radical Y is OH

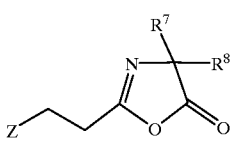

VI

Z is —S— or —NH and

R$^7$ and R$^8$ independently of one another are H or alkyl having 1–5 C atoms.

12. The shaped article according to claim 1, wherein the monomers polymerized in d) comprise monomer units of the formula III:

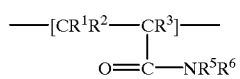

III wherein

R$^1$, R$^2$ and R$^3$ independently of one another are H or CH$_3$,

R$^4$ is H, alkyl having 1–5 C atoms which is substituted by —COOH, by —SO$_3$H, by —NR$^7$R$^8$ or by —N$^+$R$^7$R$^8$R$^9$, or aryl having 6–12 C atoms which is substituted by —COOH, by —SO$_3$H, by —NR$^7$R$^8$ or by —N$^+$R$^7$R$^8$R$^9$, R$^6$ is alkyl having 1–5 C atoms which is substituted by —COOH, by —SO$_3$H, R$^6$ is alkyl having 1–5 C atoms which is substituted by —COOH, by —SO$_3$H, by —NR$^7$R$^8$ or by —N$^+$R$^7$R$^8$R$^9$, or aryl having 6–12 C atoms which is substituted by —COOH, by —SO$_3$H, by —NR$^7$R$^8$ or by —N$^+$R$^7$R$^8$R$^9$, wherein R$^5$ and R$^6$ are coordinated such that the either both radicals are acidic or basic or at least one of the radicals is neutral, and R$^7$ and R$^8$ independently of one another are H or alkyl having 1–5 C atoms.

13. The shaped article according to claim 1, wherein the monomers polymerized in d) comprise monomer units of the formula IV:

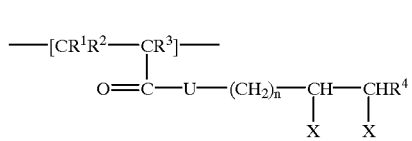

IV wherein

R$^1$, R$^2$ and R$^3$ independently of one another are H or CH$_3$,

R$^4$ is H, alkyl having 1–5 C atoms or aryl having 6–12 C atoms,

U is —O— or —NH— n is an integer from 1 to 5 and one radical X is a separation effector and the other radical X is OH.

14. The shaped article according to claim 13, wherein the separation effector for X is an ionic group selected from the group consisting of —PO$_4$H$_2$, —SO$_3$H, —NR$^7$R$^8$ or —N$^+$R$^7$R$^8$R$^9$, wherein R$^7$ and R$^8$ independently of one another are H or alkyl having 1–5 C atoms and R$^9$ is alkyl having 1–5 C atoms with the proviso that if X=—N$^+$R$^7$R$^8$R$^9$, R$^7$ and R$^8$ cannot be H.

15. The shaped article according to claim 13, wherein the separation effector for X is a hydrophobic group —OR$^{10}$ or —NHR$^{10}$, wherein R$^{10}$ is C$_1$–C$_{20}$-alkyl, C$_6$–C$_{25}$-aryl, C$_7$–C$_{25}$-alkylaryl or C$_7$–C$_{25}$-arylalkyl, and wherein these radicals can also be derivatized with nitrile or C$_1$–C$_5$-alkoxy, and wherein also one or more non-adjacent CH$_2$ groups can be replaced by NH or O, or also one or more CH groups can be replaced by N.

16. The shaped article according to claim 13, wherein the separation effector for X is a metal chelate affinity group.

17. The shaped article according to claim 13, wherein the separation effector for X is a thiophilic radical.

18. The shaped article of claim 1, wherein the article is a membrane, a sponge, a hose or a hollow fiber membrane.

* * * * *